(12) United States Patent
Asano

(10) Patent No.: US 6,659,933 B2
(45) Date of Patent: Dec. 9, 2003

(54) RADIATION SOURCE WIRE MEMBER FOR TREATING CANCER AND ITS DELIVERY APPARATUS

(75) Inventor: Yuichiro Asano, Tokyo (JP)

(73) Assignees: Asano & Associates Corporation, Tokyo (JP); Radiomed Corporation, Tyngsboro, MA (US)

( * ) Notice: Subject to any disclaimer, the term of this patent is extended or adjusted under 35 U.S.C. 154(b) by 205 days.

(21) Appl. No.: 09/729,922

(22) Filed: Mar. 26, 2001

(65) Prior Publication Data

US 2002/0004625 A1 Jan. 10, 2002

(30) Foreign Application Priority Data

Dec. 7, 1999 (JP) ............................................ 11-347530

(51) Int. Cl.[7] .............................. A61N 5/00; A61N 1/05; A61M 36/00
(52) U.S. Cl. ............................................................ 600/3
(58) Field of Search ............................ 600/1–9; 606/33, 606/27–31; 607/96–100

(56) References Cited

U.S. PATENT DOCUMENTS

| | | | | |
|---|---|---|---|---|
| 5,498,227 A | * | 3/1996 | Mawad ........................... | 600/3 |
| 5,851,206 A | * | 12/1998 | Guglielmi et al. ............ | 606/28 |
| 5,976,106 A | * | 11/1999 | Verin et al. .................... | 604/96 |
| 6,024,690 A | * | 2/2000 | Lee et al. ....................... | 600/3 |
| 6,419,621 B1 | * | 7/2002 | Sioshansi et al. .............. | 600/3 |
| 6,436,026 B1 | * | 8/2002 | Sioshansi et al. .............. | 600/3 |
| 2001/0014767 A1 | * | 8/2001 | Peterson ........................ | 600/3 |
| 2001/0027261 A1 | * | 10/2001 | Ciezki et al. .................. | 600/3 |

FOREIGN PATENT DOCUMENTS

JP    4-64368    * 2/1992

* cited by examiner

Primary Examiner—John A. Jeffery
(74) Attorney, Agent, or Firm—Browdy and Neimark

(57) ABSTRACT

A radiation source wire member for radiotherapy indwelling in cancer-affected part of the body comprises an indwelling tip end portion having a radiation source of rhodium coil wire partially converted to $^{103}$Pd, and a filament connected to the indwelling portion, the filament having such a length that at least a rear end portion thereof is exposed outside the body after indwelling in the cancer-affected part. An apparatus for delivering the radiation source wire member to the cancer-affected part of the body has a catheter structure comprising (a) an outer tube having an inner diameter permitting the indwelling portion to pass through without resistance, and (b) an inner tube received in the outer tube movably back and forth therein and having an inner diameter not permitting the indwelling portion to pass through but permitting the filament to pass through without resistance.

19 Claims, 3 Drawing Sheets

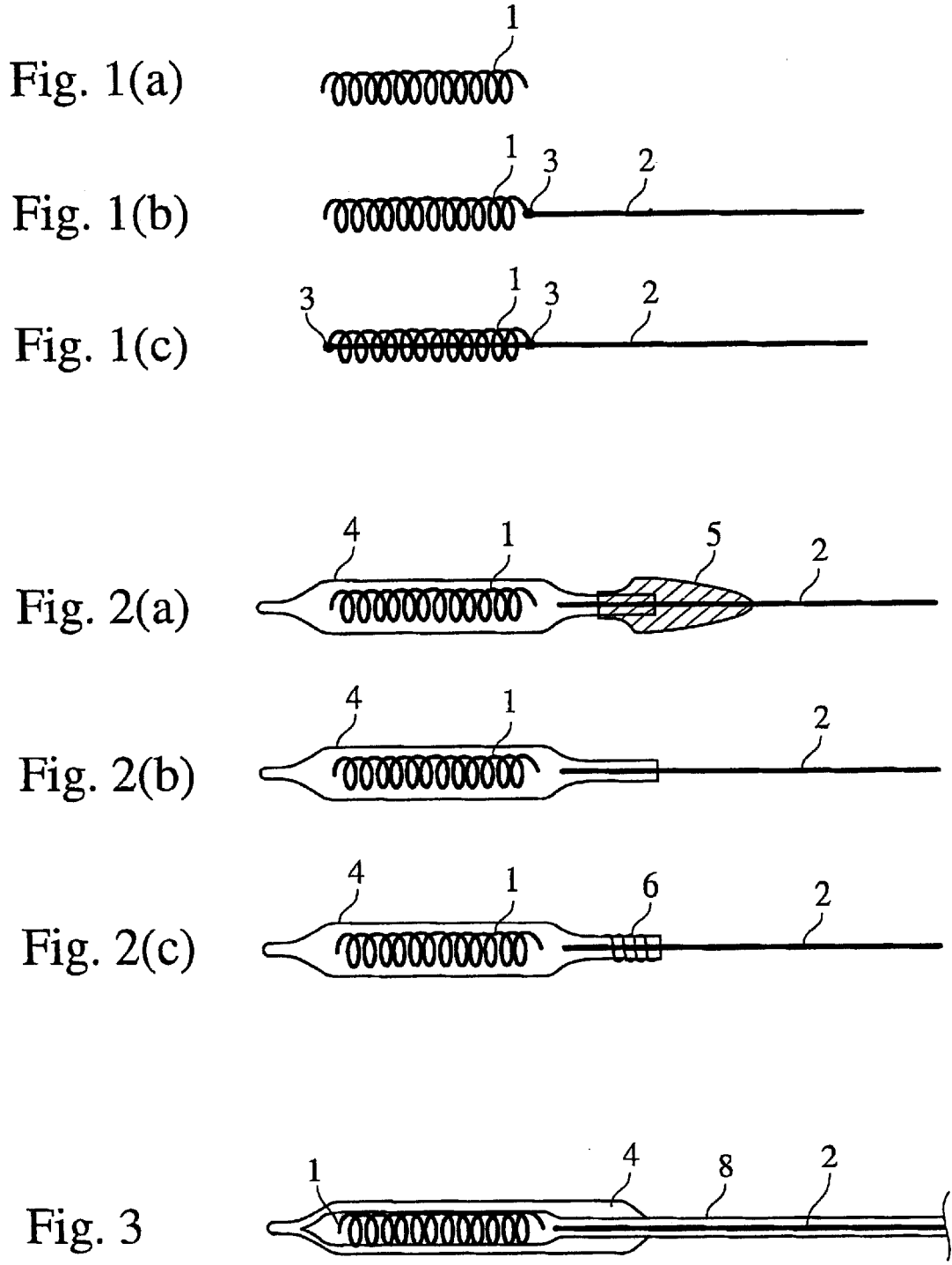

RADIATION SOURCE WIRE MEMBER FOR TREATING CANCER AND ITS DELIVERY APPARATUS

FIELD OF THE INVENTION

The present invention relates to a radiation source wire member and its delivery apparatus effective in radiotherapy of cancers and tumors such as prostate cancer, breast cancer, etc.

BACKGROUND OF THE INVENTION

The number of prostrate cancer patients has been increasing rapidly in Japan because of the recent Westernization of lifestyle and diet. Though the prostrate cancer is likely to provide such symptoms as urination disorder and hematuria, there are so many cases exhibiting no symptoms that it is difficult to find it out at an early stage.

The prostate cancer may be cured by the ablation of the affected part and a radiation therapy. However, the former treatment inficts large pain on the patients, while the latter treatment gives anxiety to them because the other organs are unnecessarily exposed to radiation.

Against this treatment, much attention has recently been paid to a close-distance radiation therapy (brachytherapy), by which the cancer-affected part of the body is treated by radiation from a source disposed close thereto. This method utilizes direct, low-energy radiation to the affected part, making patients feeling safe without pain as in surgical operation.

The latest brachytherapy in the U.S. uses radioactive seeds for low-energy radiation with $^{125}$I or $^{103}$Pd as a radiation nuclide.

FIG. 6(a) shows an example using $^{103}$Pd as a radiation nuclide, in which a radiation seed comprising graphite pellet 25 coated with $^{103}$Pd and an X-ray marker 23 made of lead is encapsulated in a titanium tube 20 of 0.8 mm in diameter and 4.5 mm in length with sealed ends.

FIG. 6(b) shows an example using $^{125}$I as a radiation nuclide, wherein a silver bar24 coated with $^{125}$I is encapsulated in a titanium tube 20 of 0.8 mm in diameter and 4.5 mm in length like FIG. 6(a). In the examples shown in FIGS. 6(a) and (b), these capsules are usually connected at a uniform interval to provide a train-connected radiation source, because of difficulty in the direct or accurate insertion into the cancer-affected part of the body. See FIG. 5(b).

However, this radiation source is disadvantageous not only in complicated structure and high production cost, but also in low radiation efficiency because radiation is effected through the titanium capsule. As shown in FIG. 5(b), the use of a train-connected radiation source results in nonuniform radiation onto the affected part of the body. In addition, because of a large diameter of a delivery needle (outer diameter: 1.9 mm), the body tissues are likely to be deformed or damaged.

Accordingly, it is optimum to use a radiation source in the form of a coiled wire low at production cost and excellent in radiation distribution, which is now under development, and a radiation means high in radiation efficiency and uniform in radiation distribution is obtained by subjecting a rhodium wire to a proton activation treatment to partly convert Rh to $^{103}$Pd, the activated rhodium wire being most desirably formed into a coil.

OBJECT OF THE INVENTION

Accordingly, an object of the present invention is to provide a radiation source wire member effective for the brachytherapy of cancer and tumor such as prostate cancer, breast cancer, etc., particularly to a radiation source wire member comprising a radiation source constituted by a coiled wire of rhodium at least partly converted to $^{103}$Pd.

Another object of the present invention is to provide a delivery apparatus for indwelling the radiation source wire member in the cancer-affected part of the body.

SUMMARY OF THE INVENTION

As a result of intensive research in view of the above objects, the inventors have found that by using a coiled wire of rhodium partly converted to $^{103}$Pd as a radiation source wire member, and by inserting this member in a capsule if necessary, and further by charging it into a tubular delivery apparatus for brachytherapy, the member can be indwelled in the cancer-affected part of the body rapidly and accurately. The present invention is completed based on this finding.

The first radiation source wire member indwelling in the cancer-affected part of the body for radiotherapy according to the present invention comprises an indwelling tip end portion having a radiation source and a filament bonded to the indwelling portion, the filament having such a length that at least a rear end portion thereof is exposed outside the body after indwelling.

The second radiation source wire member according to the present invention comprises an indwelling tip end portion having a radiation source and a filament covered with a synthetic resin capsule, a rear end of the capsule being bonded to the filament having such a length that at least a rear end of portion thereof is exposed outside the body after indwelling.

The first apparatus for delivering the radiation source wire member to the cancer-affected part of the body for indwelling according to the present invention has a catheter structure comprising (a) an outer tube having an inner diameter permitting the indwelling portion to pass through without resistance, and (b) an inner tube received in the outer tube movably back and forth therein and having an inner diameter not permitting the indwelling portion to pass through but permitting the filament to pass through without resistance.

The second delivery apparatus for delivering the radiation source wire member to the cancer-affected part of the body for indwelling according to the present invention comprises a tube having an inner diameter permitting the radiation source wire member to pass through without resistance, and a plunger movably received in the tube for pushing the radiation source wire member out of a tip end of the tube.

The indwelling tip end portion has a radiation source preferably constituted by a coil of rhodium at least partially converted to $^{103}$Pd by a proton activation treatment.

BRIEF DESCRIPTION OF THE DRAWINGS

FIG. 1(a) is a schematic view showing a coiled rhodium wire as a radiation source wire member;

FIG. 1(b) is a schematic view showing a coiled rhodium wire connected to a filament;

FIG. 1(c) is a schematic view showing a filament connected to a tip end of the coiled rhodium wire and passing through the inside of the coiled rhodium wire;

FIG. 2(a) is a schematic view showing an example that a tip end portion of the radiation source wire member is embedded in a capsule bonded to the filament by caulking;

FIG. 2(b) is a schematic view showing a capsule fused to the filament;

FIG. 2(c) is a schematic view showing a capsule fused to the filament,

FIG. 3 is a schematic view showing another example in which a tip end portion of the radiation source wire member is covered with a capsule;

BEST MODE FOR CARRYING OUT THE INVENTION

[1] Radiation Source Wire Member

The radiation source wire member of present invention comprises an indwelling portion 1 positioned in the cancer-affected part of the body for brachytherapy of prostrate cancer, etc., and a filament 2 connected to the indwelling portion 1.

(1) Indwelling Portion

The indwelling portion 1 at the tip end of the radiation source wire member of the present invention is constituted by a wire of rhodium at least partly converted to $^{103}$Pd, a radioisotope in the form of a coil as shown in FIG. 1(a). The rhodium wire has a diameter of preferably 0.03 mm to 0.1 mm, more preferably 0.04 mm to 0.06 mm. When the diameter of the rhodium wire is as small as less than 0.03 mm, it is too thin to be worked and easily cut. On the other hand, when the diameter of the rhodium wire is more than 0.1 mm, the wire is too thick, undesirably poor in flexibility in the form of a coil.

The outer diameter of the coil is preferably 0.2 mm to 0.5 mm. When the outer diameter of the coil is less than 0.2 mm, the coil is too thin to be worked. On the other hand, when the outer diameter of the coil is more than 0.5 mm, the coil is so thick that it gives a patient the feeling of having a foreign matter in the body when indwelling, and that it undesirably enlarges the outer diameter of a delivery needle, a tip end portion of the delivery apparatus of the present invention. The more preferable outer diameter of the coil is 0.3 mm to 0.4 mm.

Figure 5A:
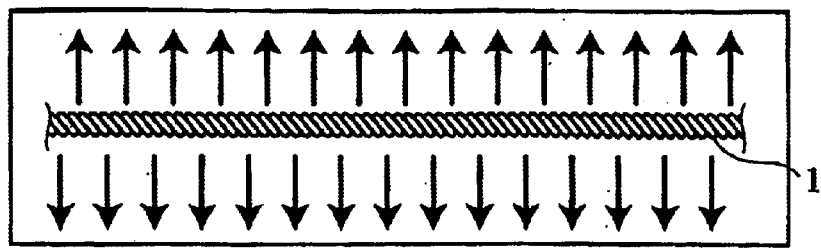
FIG. 5(a) is a schematic view showing a coiled radiation source wire according to the present invention.
Figure 5B:
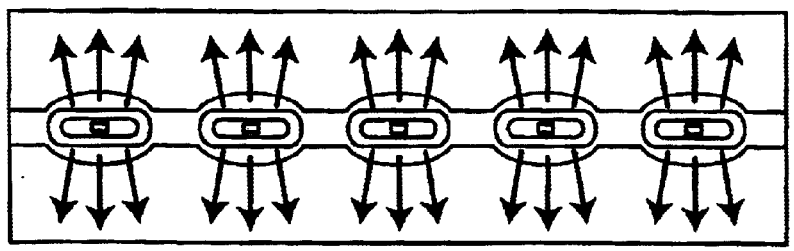
FIG. 5(b) is a schematic view showing a conventional train-connected radiation source.
Figure 6A:
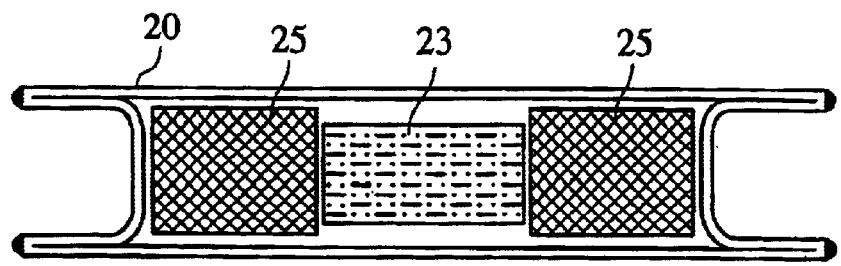
FIG. 6(a) is a schematic cross-sectional view showing a conventional radiation seed using $^{103}$Pd as a radiation nuclide.
Figure 6B:
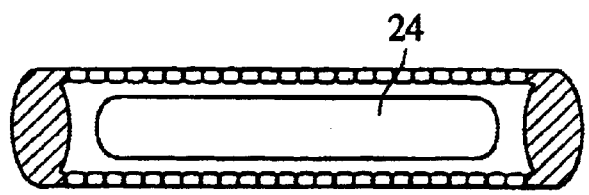
FIG. 6(b) is a schematic cross-sectional view showing a conventional radiation seed using $^{125}$I as a radiation nuclide.

The coiled wire radiation source (indwelling portion 1) partially converted to $^{103}$Pd is simpler in structure and thus lower in production cost than those of the conventional radiation wires as shown in FIGS. 6(a) and (b), and is higher in radiation efficiency than the latter because of direct irradiation to the affected part of the body. In addition, because the radiation source is in the form of a longitudinally uniform coil as shown in FIG. 5(a), it can provide a uniform radiation distribution unlike the conventional train-formed radiation source shown in FIG. 5(b). Further, because the coiled wire radiation source has a delivery needle of such a small outer diameter as 0.7 mm, it is less likely to deform or damage the body tissue during insertion, effective for brachytherapy in prostate cancer and the like.

(2) Filament

Though the radiation source wire member would not need a filament 2 if left permanently inside the body, a filament 2 may be connected to an end of the indwelling portion 1 (coiled wire), if the indwelling portion 1 is recoverable. The filament 2 is preferably a wire of metals such as stainless steel and titanium or a stitch, with a diameter of 0.1 mm to 0.2 mm. When the diameter of the filament is less than 0.1 mm, it is so thin that it is easily cut. On the other hand, when the diameter of the filament is more than 0.2 mm, the filament is not preferable for practical use. The filament 2 preferably has such a length that at least a tail thereof exposes outside the body after the indwelling portion 1 is positioned in the affected part of the body.

(3) Examples of Radiation Source Wire Member (a) First Example

The first example of the radiation source wire member of the present invention has a structure in which the indwelling coiled wire portion 1 is directly connected to the filament 2 by spot welding or laser welding as shown in FIGS. 1(b) and (c). The radiation source wire member may have a welded portion 3 not only at a rear end of the indwelling portion 1 as shown in FIG. 1(b), but also at both tip and rear ends as shown in FIG. 1(c). The indwelling coiled wire portion 1 is so flexible that it may be reinforced for accurate positioning of the indwelling portion. In this case, the filament 2 preferably passes through the coiled wire, as shown in FIG. 1(c).

(b) Second Example

The second example of the radiation source wire member of the present invention has an indwelling portion 1 covered with a synthetic resin capsule 4, as shown in FIGS. 2(a)–(c). The capsule 4 is useful not only for fixing the indwelling portion 1 but also for connecting the indwelling portion 1 to the filament 2. A tip end portion of the capsule 4 is preferably heat-seated. The indwelling portion 1 and the filament 2 may be connected to each other, though they are not connected in the examples shown in FIGS. 2(a)–(c).

In the example shown in FIG. 2(a), a rear end of the capsule 4 is connected by caulking to a fitting metal 5 attached to the filament 2. In an example of FIG. 2(b), the rear end of the capsule 4 is fused to the filament 2. Further in the example of FIG. 2(c), a wire 6 is wound around a fused portion of the rear end of the capsule 4 and the filament 2.

(c) Third Example

In the third example of the radiation source wire member of the present invention, the filament 2 has a synthetic resin cover 8 as shown in FIG. 3. The indwelling portion 1 is coated with a synthetic resin capsule 4 like the second example, easily fusible with the synthetic resin cover 8.

[2] Delivery Apparatus (1) First Delivery Apparatus

Figure 4A:
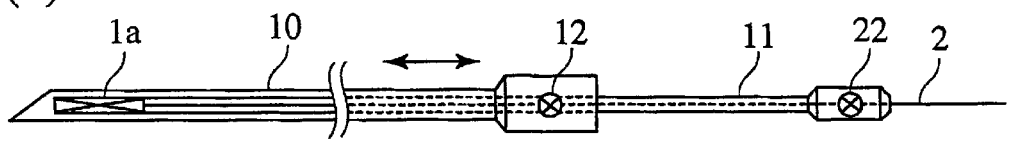
FIG. 4(a) is a schematic cross-sectional view showing an example of a delivery apparatus having an outer tube and an inner tube according to the present invention.

As shown in FIG. 4(a), the first delivery apparatus of this invention has a catheter structure comprising an outer tube 10 having an inner diameter permitting the indwelling portion 1a to pass through without resistance and movably received in the outer tube 10, and an inner tube 11 received in the outer tube movably back and forth therein and having an inner diameter not permitting the indwelling portion 1a to pass through but permitting the filament 2 to pass through without resistance. The outer tube 10 and the inner tube 11 are provided with stoppers 12 and 22, respectively, to stop the inner tube 11 and the filament 2.

As shown in FIG. 4(a), with the indwelling portion 1a loaded in the outer tube 10, the filament 2 is fixed by the stopper 22 mounted onto the inner tube 11, and the inner tube 11 is fixed by the stopper 12 mounted onto the outer tube 10. In this state, the first delivery apparatus is inserted into the cancer-affected part of the body. Because the indwelling portion 1a is loaded in the delivery apparatus, it does not suffer from deformation due to power from outside during delivery into the cancer-affected part of the body. After the indwelling portion 1a is inserted into the cancer-affected part of the body at a predetermined position, the stopper 12 is loosened while keeping the stopper 22 tight, and the outer tube 10 is withdrawn with the inner tube 11 fixed, until the indwelling portion 1a is exposed from the outer tube 10. Next, the stopper 22 is loosened with the stopper 12 fixed, followed by withdrawal of both the inner tube 11 and the outer tube 10. The indwelling portion 1a is thus rested in the cancer-affected part of the body while leaving the filament 2 connected thereto in the body. Because the filament 2 is longer than the indwelling length, a tail of the filament 2 is exposed outside the body.

With the above-described mobile structure, high operation efficiency is achieved when the radiation source wire member is inserted into or withdrawn from the cancer-affected part of the body. With respect to the structure of the indwelling portion 1a, those without a capsule structure may also be used in the delivery apparatus of the present invention.

(2) Second Delivery Apparatus

Figure 4B:
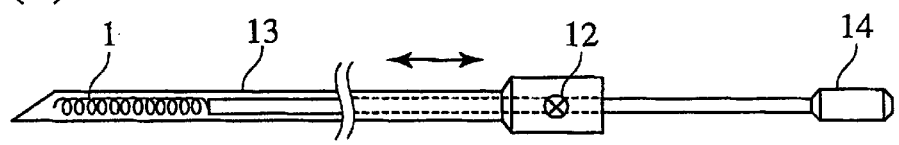
FIG. 4(b) is a schematic cross-sectional view showing a delivery apparatus having a plunger for indwelling the coiled rhodium wire to the cancer-affected part of the body.

The second delivery apparatus of the present invention functioning to deliver only the indwelling portion 1 shown in FIG. 1(a) in the cancer-affected part of the body, comprises a tube 13 having an inner diameter permitting the indwelling portion 1 to pass through without resistance, a plunger 14 movably received in the tube 13 for indwelling portion 1 in the cancer-affected part of the body with stability, and a stopper 12 for stopping the plunger 14, as shown in FIG. 4(b).

In this example, with the indwelling portion 1 loaded in the tube 13, the plunger 14 engages the stopper 12 such that a tip end of the plunger 14 is in contact with a rear end of the indwelling portion 1. After this delivery apparatus is inserted into the cancer-affected part of the body in this state, the stopper 12 is loosened, and only the tube 13 is withdrawn while the plunger 14 is stationary. After the indwelling portion 1 is exposed from the tube 13, the stopper 12 is tightened to withdraw both the tube 13 and the plunger 14. The indwelling portion 1 is protected in the tube 13 from outside power until the second delivery apparatus is withdrawn, ensuring that the indwelling portion 1 is put in the affected part of the body safely and easily while preventing deformation and damage thereof.

Figure 4C:
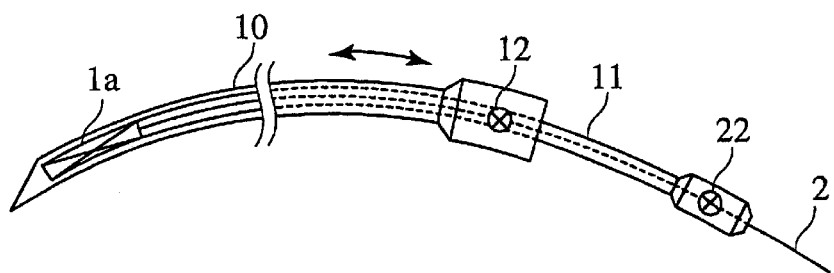
FIG. 4(c) is a schematic cross-sectional view showing a curved delivery apparatus having an outer tube and an inner tube according to the present invention.

Tip ends of the first and second delivery apparatuses are preferably in a slantingly cut shape. If each delivery apparatus has a curved overall structure as shown in FIG. 4(c), it can easily be inserted into the cancer-affected part of the body to put a radiation source wire member at a predetermined position therein, into which insertion is difficult with a linear delivery apparatus.

As described in detail above, the radiation source wire member of the present invention is suitable for use in brachytherapy for the cancer, alleviating the patients' physical and mental pain in treatment. Further, with the above-described delivery apparatus of the present invention, high treatment efficiency is achieved because the radiation source wire member is indwelled stably and accurately.

What is claimed is:

1. A radiation source wire member indwelling in a cancer-affected part of the body for treating said cancer with irradiation, said wire member comprising an indwelling tip end portion having a radiation source and covered by a synthetic resin capsule, and a filament bonded to a rear end of said capsule.

2. The radiation source wire member according to claim 1, wherein said indwelling portion is a rhodium coil, at least partially converted to $^{103}$Pd by a proton activation treatment.

3. The radiation source wire member according to claim 2, wherein said coil is spot-welded or laser-welded to said metal wire.

4. The radiation source wire member according to claim 1, wherein said filament is a metal wire or a stitch.

5. An apparatus for delivering a radiation source wire member for indwelling within a cancer-affected part of the body for treating said cancer with irradiation, said wire member comprising an indwelling tip end portion having a radiation source and a filament bonded to said indwelling portion, said filament having such length that at least a rear end portion of said filament is exposed outside the body after indwelling, said apparatus for delivering having a catheter structure comprising (a) an outer tube having an inner diameter permitting said indwelling portion to pass through without resistance, and (b) an inner tube received in said outer tube movably back and forth therein and having an inner diameter not permitting said indwelling portion to pass through but permitting said filament to pass through without resistance.

6. The delivery apparatus according to claim 5, wherein said outer tube is provided with a stopper for engaging said inner tube, and said inner tube is provided with a stopper for engaging said filament.

7. The delivery apparatus according to claim 5, wherein a tip end of a tube for receiving said radiation source wire member has a shape obtained by oblique cutting in one direction.

8. The delivery apparatus according to claim 5, wherein an entire body of said delivery apparatus is curved.

9. An apparatus for delivering a radiation source wire member for indwelling within a cancer-affected part of the body for treating said cancer with irradiation, said wire member comprising an indwelling tip end portion having a radiation source and a filament bonded to said indwelling portion, said filament having such a length that at least a rear end portion of said filament is exposed outside the body after indwelling, said apparatus for delivering having a catheter structure comprising (a) an outer tube having an inner diameter permitting said indwelling portion to pass through without resistance, and (b) an inner tube received in said outer tube movably back and forth therein and having an inner diameter not permitting said indwelling portion to pass through but permitting said filament to pass through without resistance, wherein the radiation source wire member is adapted to deliver radiation to a prostate gland as the cancer-affected part.

10. The radiation source wire member according to claim 1, wherein said indwelling tip end portion has the form in a coil having an outer diameter of 0.2 mm to 0.5 mm and said filament has a diameter of 0.1 mm to 0.2 mm.

11. A radiation source wire member indwelling in a cancer-affected part of the body for treating said cancer with irradiation, said wire member comprising an indwelling tip end portion having a radiation source and covered by a synthetic resin capsule, and a filament bonded to a rear end of said capsule, wherein said filament has a diameter of 0.1 mm to 0.2 mm.

12. The radiation source wire member according to claim 11, wherein said indwelling portion is at least partially converted to $^{103}$Pd.

13. The radiation source wire member according to claim 11, wherein said filament is a metal wire or a stitch and has such a length that at least a rear end portion of said filament is exposed outside the body after indwelling.

14. A radiation source wire member indwelling in a cancer-affected part of the body for treating said cancer with irradiation, said wire member comprising an indwelling tip end portion having a radiation source and covered by a synthetic resin capsule, and a filament bonded to a rear end of said capsule, wherein a rear end of said capsule is bonded by caulking to a connecting metal member fixed to said filament.

15. The radiation source wire member according to claim 11, wherein a rear end of said capsule is fused to said filament.

16. A radiation source wire member indwelling in a cancer-affected part of the body for treating said cancer with irradiation, said wire member comprising an indwelling tip end portion having a radiation source and covered by a synthetic resin capsule, and a filament bonded to a rear end of said capsule, wherein said filament is a metal wire covered by a synthetic resin, and said capsule of said indwelling tip end portion is fused to said synthetic resin cover of said filament.

17. An apparatus for delivering a radiation source wire member comprising a rhodium coil at least partially converted to $^{103}$Pd to a cancer-affected part of the body for indwelling, said delivery apparatus comprising a tube having an inner diameter permitting said radiation source wire member to pass through without resistance, and a plunger movably received in said tube for pushing said radiation source wire member out of a tip end of said tube.

18. The delivery apparatus according to claim 17, wherein a tip end of said tube for receiving said radiation source wire member has a shape obtained by oblique cutting in one direction.

19. The apparatus for delivering a radiation source wire member according to claim 17, wherein said rhodium wire has a diameter of 0.2 mm to 0.5 mm.

* * * * *